United States Patent [19]
Crooks

[11] 3,947,487
[45] Mar. 30, 1976

[54] MANUFACTURE OF ORGANIC NITRILES

[75] Inventor: Graham Robert Crooks, Billingham, England

[73] Assignee: Imperial Chemical Industries Ltd., London, England

[22] Filed: Oct. 11, 1974

[21] Appl. No.: 514,315

[30] Foreign Application Priority Data
Jan. 17, 1974 United Kingdom.............. 2194/74

[52] U.S. Cl...................... 260/465.3; 260/456.8 R
[51] Int. Cl.².................................... C07C 120/02
[58] Field of Search........ 260/465.3, 465.8 R, 465.9

[56] References Cited
UNITED STATES PATENTS

| | | | |
|---|---|---|---|
| 2,385,741 | 9/1945 | Teter............................. | 260/465.3 |
| 2,422,859 | 6/1947 | Schulze et al................ | 260/465.3 X |
| 2,464,723 | 3/1949 | Schulze et al................ | 260/465.3 |
| 2,509,859 | 5/1950 | Coffman et al................ | 260/465.3 |
| 2,553,008 | 5/1951 | Sager............................ | 260/465.3 |
| 3,711,527 | 1/1973 | Kurtz............................ | 260/465.8 |
| 3,836,567 | 9/1974 | Krekeler et al................ | 260/465.9 |
| 3,849,472 | 11/1974 | Waddan........................ | 260/465.3 |

*Primary Examiner*—Joseph P. Brust
*Attorney, Agent, or Firm*—Cushman, Darby & Cushman

[57] ABSTRACT

Olefins are converted to nitriles by reacting with hydrogen cyanide in the presence of an organic thiol or sulphide and a catalytic amount of a cuprous salt which is soluble therein; especially for making 3-pentene nitrile from butadiene.

7 Claims, No Drawings

MANUFACTURE OF ORGANIC NITRILES

This invention relates to the manufacture of organic nitriles and, more particularly, to their manufacture by reaction of olefinic compounds with hydrogen cyanide in the presence of a catalyst.

Our invention provides a process for the manufacture of organic nitriles which comprises reacting an olefin with hydrogen cyanide in the presence of an organic thiol or sulphide and a catalytic amount of a cuprous salt which is soluble in the said thiol or sulphide.

The cuprous salt which is soluble in the thiol or sulphide is preferably cuprous chloride or bromide.

The class of organic thiols or sulphides includes organic compounds which contain the groupings —SH or —S—, where the valencies shown are attached to carbon atoms. The class includes in particular compounds of the formulae:

$$R_1SH \text{ and } R_1SR_2$$

in which $R_1$ and $R_2$ are aliphatic, cycloaliphatic, araliphatic or aromatic radicals, and, in the case of sulphides, may be the same or different, and may be joined to form, with the S atom, a heterocyclic ring containing sulphur. The radicals $R_1$ and $R_2$ may carry substituents, for example hydroxyl, alkoxyl, carboxylic ester and halogen substituents, and the aliphatic and cycloaliphatic radicals they represent may contain carbon-carbon unsaturation, especially ethylene unsaturation. Moreover, the heterocyclic rings containing the S atom may contain carbon-carbon unsaturation and may contain other hetero atoms, especially nitrogen, oxygen or sulphur atoms. Preferably the heterocyclic rings have 5, 6 or 7, especially 5 or 6, atoms in the ring.

Especially suitable organic thiols and sulphides include those of the above general formulae in which $R_1$ and $R_2$ represent alkyl groups having from 1 to 6 carbon atoms and, in the case of sulphides, may be the same or different, especially the same. Also especially suitable are thiophen and sulphides of the above general formulae in which $R_1$ and $R_2$ together represent tetramethylene or pentamethylene groups. As examples of such especially suitable compounds there may be mentioned methyl mercaptan, ethyl mercaptan, propyl mercaptan, butyl mercaptan, amyl mercaptan, hexyl mercaptan, dimethyl sulphide, diethyl sulphide, dipropyl sulphide, dibutyl sulphide, diamyl sulphide, dihexyl sulphide, methyl ethyl sulphide, thiophen, tetrahydrothiophen and pentamethylene sulphide.

Other suitable compounds include cyclohexyl-mercaptan, benzyl mercaptan, thiophenol, dicyclohexyl sulphide, dibenzyl sulphide, diphenyl sulphide, ditolyl sulphide, thiodiglycol and thiomorpholine.

The organic thiol or sulphide may form a complex with the cuprous salt. In any event it is preferred that the thiol or sulphide is used in at least stoichiometric amount in relation to the copper. Substantially more than the stoichiometric amount may be used, however. It is preferred that the cuprous salt is dissolved in the minimum amount of the thiol or sulphide. Thus, for example, for each part by weight of cuprous salt there may be used from 0.5 to 5 parts by weight of thiol or sulphide, to give a solution.

The process of our invention may be carried out over a wide range of temperatures, for example from −25° to 200°C. Because of decay of catalyst at higher temperatures, however, and because of the low rate of reaction at lower temperatures it preferred to operate in the temperature range 50° to 160°C, and more preferably from 90° to 135°C, temperatures of about 120°C being very suitable. Owing to the volatility and toxicity of hydrogen cyanide the reaction is preferably conducted in a closed vessel under autogenous pressure or, if desired, under deliberately raised pressure, for example at a pressure of from 1 to 50 atmospheres. If desired a solvent may be used, for example a hydrocarbon solvent such as benzene, toluene or xylene or a nitrile solvent such as acetonitrile, propionitrile, benzonitrile or adiponitrile. Agitation of the reactants is desirable. The reaction is continued for a time sufficient to give a suitable conversion. In the case of a batch process the time will normally be for from 1 hour up to a period of several days, for example 5 days.

The olefin and the hydrogen cyanide may be used in equimolar proportions or an excess of either may be used, especially within the molar range of olefin to hydrogen cyanide of 2 : 1 to 1 : 10. The cuprous salt is used in catalytic amount: this will normally fall within the range 0.0005 to 0.1 mole per mole of olefin. We prefer that the proportion of the said salt is from 0.005 to 0.05 mole per mole of olefine.

The organic nitrile formed in the process may be separated from the reaction mixture by first removing any excess olefin and/or hydrogen cyanide by distillation or by simply venting the apparatus. The organic nitrile may then be separated from cuprous salt residues and organic thiol or sulphide, by conventional methods such as filtration with or without extraction with solvent, or by distillation. The process may readily be adapted to continuous operation.

The process of our invention is particularly valuable for the monohydrocyanation of butadiene to 3-pentene nitrile. In certain circumstances bis-hydro-cyanation to give adiponitrile may occur.

U.S. Pat. No. 2,509,859 describes the reaction of butadiene and hydrogen cyanide in the presence of, for example, cuprous chloride, to give 3-pentene nitrile. Although the reaction is described as catalytic good yields of 3-pentene nitrile are obtained only if substantially equimolar proportions of butadiene and cuprous salt are used. With catalytic proportions, for example 0.006 moles of cuprous chloride per mole of butadiene, both the conversion of butadiene and the yield of 3-pentene nitrile are low. In the process of our invention, however, catalytic amounts of cuprous salt, when used in conjunction with an organic thiol or sulphide, give good conversions of butadiene and good yields of 3-pentene nitrile.

It has already been proposed to react butadiene and hydrogen cyanide in the presence of catalytic amounts of certain catalysts, for example certain zerovalent nickel catalysts, as described, for example, in United Kingdom patent specification No. 1,104,140. Such processes give mixtures of linear pentene nitriles, which are convertible by further reaction with hydrogen cyanide into adiponitrile, and branched methyl butene nitriles which cannot be converted directly into adiponitrile. The proportion of linear pentene nitriles compared with branched methyl butene nitriles produced in such processes is not normally greatly in excess of 70% by weight (or molar). It is an advantage of the process of our invention that the proportion of linear 3-pentene nitrile, directly convertible to adiponitrile, which is produced is much higher, usually at least 80% by weight (or molar), that is the ratio of 3-pentene nitrile to branched methyl butenenitriles is at least 4 : 1. Moreover, the zero-valent nickel catalysts used in the prior process are sensitive to moisture whereas the catalysts used in the process of our present invention are not. Thus, anhydrous conditions are not required and it is not therefore necessary, for example, to specially dry the olefin and hydrogen cyanide.

3-Pentene nitrile is particularly valuable for further reaction with hydrogen cyanide in the presence of a catalyst to give adiponitrile. Adiponitrile may be hydrogenated to hexamethylene diamine, a valuable intermediate for polycondensation with dicarboxylic acids to give polyamides, especially, for example, with adipic acid to give polyhexamethylene adipamide (nylon 6,6), a well-known polyamide for use in the manufacture of mouldings and for melt spinning into synthetic fibres.

The invention is illustrated but not limited by the following Examples.

EXAMPLE 1

A mixture of 30 ml. (19.5 g.) of butadiene, 15 ml. of hydrogen cyanide, and a solution of 1.8g. of anhydrous cuprous chloride in 3 ml. of thiophen was heated at 120°C in a closed vessel for 17 hours. After removing excess butadiene and hydrogen cyanide by evaporation, the product liquor (22.8g.) was distilled to give a first fraction (1.7 g.) consisting mainly of low boiling material, including thiophen, but which was found to contain 4.1% (0.07 g.) of 3-pentene nitrile, and a second fraction (14.2 g.) which was found to contain 74.5% (10.1 g.) of 3-pentene nitrile and 6.7% (0.9 g.) of 2-methyl-3-butene nitrile. The residue was 4.7 g. The conversion of butadiene to mononitriles was 40% and the yield of 3-pentene nitrile calculated on the butadiene so converted was 91.6% and of 2-methyl-3-butene nitrile 8.4%.

EXAMPLE 2

A mixture of 10.4 g. of butadiene, 7 ml. of hydrogen cyanide and a solution of 1.2 g. of anhydrous cuprous chloride in 2 ml. of di-n-propyl sulphide was heated at 145°C in a closed vessel for 17 hours. After removing excess butadiene and hydrogen cyanide by evaporation the product liquor (14.6 g.) was distilled giving 11.34g. of distillate and leaving a residue of 2.11 g. The distillate was found to contain 66% (7.48g.) of 3-pentene nitrile and 3.7% (0.42g.) of 2-methyl-3-butene nitrile. The conversion of butadiene to mononitriles was 50.6% and the yield of 3-pentene nitrile calculated on the butadiene so converted was 94.8% and of 2-methyl-3-butene nitrile 5.2%.

EXAMPLE 3

Anhydrous cuprous chloride (0.6 g.) was dissolved in 0.9 ml. of di-n-propyl sulphide (or the compound specified in the Table) and the solution introduced into a tube filled with nitrogen. After purging with nitrogen, 5 ml. of hydrogen cyanide, redistilled from phosphorus pentoxide, were condensed into the tube at −78°C. 10 ml. of butadiene, purified by passage through an ion exchange column, were then distilled into the tube which was then sealed. The mixture was then stirred magnetically and heated to the operating temperature for the operating period (see Table). The tube was then cooled to −78°C and opened. Unreacted butadiene and hydrogen cyanide were distilled off and the remaining liquor filtered from solid catalyst. The liquor was then analysed by gas-liquid chromatography for 3-pentene nitrile 2-methyl-3-butene nitrile and adiponitrile.

| Compound | Reaction Conditions | | Proportions in Product Liquor: wt.% | | | Ratio: 3-pentene nitrile: 2-methyl-3-butene nitrile |
|---|---|---|---|---|---|---|
| | Temp. °C | Time Hrs. | 3-pentene nitrile | 2-methyl-3-butene nitrile | Adiponitrile | |
| Dimethyl sulphide | 100 | 17 | 24.5 | 1.7 | — | 14.3 |
| Diethyl sulphide | 100 | 17 | 23.6 | 1.99 | — | 11.85 |
| Di-n-propyl sulphide | 100 | 17 | 33.7 | 4.52 | — | 7.45 |
| -do- | 130 | 17 | 57.1 | 3.24 | — | 17.5 |
| -do- | 145 | 17 | 64.6 | 5.48 | — | 11.8 |
| Di-isoamyl sulphide | 100 | 17 | 16.0 | — | — | — |
| Diphenyl sulphide | 100 | 17 | 20.3 | 1.23 | — | 16.5 |
| Thiodiglycol | 100 | 17 | 2.4 | — | 3.0 | — |
| -do- | 100 | 26 | 7.9 | — | 3.6 | — |
| Thiophen | 100 | 17 | 56.4 | 4.16 | 0.95 | 13.6 |
| -do- | 160 | 17 | 56.0 | 6.2 | trace | 9.05 |
| Thiophenol | 100 | 17 | 24.5 | trace | 3.4 | — |
| Di-nOpropyl sulphide | 65 | 17 | 17.8 | 4.8 | 1.5 | 3.72 |

EXAMPLE 4

Anhydrous cuprous chloride (0.6 g.) was dissolved in 1 ml. of di-n-propyl sulphide in a tube filled with nitrogen and 8.2 g. of isoprene were introduced. After purging with nitrogen, 5 ml. of hydrogen cyanide, distilled from phosphorus pentoxide, were introduced and the tube sealed. The mixture was then stirred magnetically and heated at 110°C for 17 hours. After cooling, the tube was opened, excess volatile material distilled off and the residue distilled to give 8.2 g. of mononitriles (71.7% conversion of isoprene), over 95% of which was 4-methyl-3-pentenenitrile.

EXAMPLE 5

In an experiment conducted similarly to that in Example 4 except that the reactants were 1.74 g. of anhydrous cuprous bromide, 2 ml. of di-n-propyl sulphide, 13 g. of butadiene and 10 ml. of hydrogen cyanide, and heating was conducted for 14 hours at 100°C, the conversion of butadiene to mononitriles was 14.5%, and 3-pentenenitrile was obtained as the product in a yield of 95% calculated on the butadiene converted.

EXAMPLE 6

In an experiment conducted similarly to that in Example 4 except that the reactants were 0.6 g. of anhydrous cuprous chloride, 1.0 g. of dibenzyl sulphide, 6 g. of butadiene and 5 ml. of hydrogen cyanide, and the heating was conducted for 4 hours at 100°C, a yellow product was obtained yielding 4.45 g. of mononitriles on distillation (49.4% conversion of butadiene) consisting of 3-pentenenitrile (94.2%) and 2-methyl-3-butene-nitrile (5.8%).

EXAMPLE 7

In an experiment conducted similarly to that in Example 4 except that the reactants were 0.8 g. of anhydrous cuprous bromide, 1 ml. of thiophen, 6.5 g. of butadiene and 5 ml. of hydrogen cyanide, and heating was continued for 17 hours at 100°C the conversion of butadiene to mononitriles was 48%, and 3-pentenenitrile was obtained in a yield of 82.2% and 2-methyl-3-butene-nitrile in a yield of 17.8% calculated on the butadiene converted.

EXAMPLE 8

In an experiment conducted similarly to that in Example 4 except that the reactants were 0.6 g. of anhydrous cuprous chloride, 1 g. of dibenzyl sulphide, 8 g. of isoprene and 5 ml. of hydrogen cyanide, and heating was continued for 20 hours at 140°C, the liquid product was filtered from solid catalyst and distilled to give 4.93 g. of 4-methyl-3-pentenenitrile, b.pt. 158°–162°C of greater than 97% purity. The conversion of isoprene was 44.1%.

I claim:

1. A process for the conversion of butadiene or isoprene to 3-pentenenitrile or 4-methyl-3-pentenenitrile respectively which comprises reacting the butadiene or isoprene with hydrogen cyanide in the molar ratio of said butadiene or isoprene to hydrogen cyanide of 2:1 to 1:10 at −25° to 200°C and pressures up to 50 atmospheres in presence of from 0.0005 to 0.1 mole per mole of butadiene or isoprene of anhydrous cuprous chloride or anhydrous cuprous bromide and, for each part by weight of said cuprous chloride or cuprous bromide, of from 0.5 to 5 parts by weight of a thiol or sulphide of the formula $R_1SH$ or $R_1SR_2$ in which $R_1$ and $R_2$ represent alkyl groups having from 1 to 6 carbon atoms, said alkyl being unsubstituted or substituted by hydroxyl, alkoxyl, carboxylic ester or halogen, or represent cyclohexyl, phenyl, tolyl or benzyl groups, or together with the S atom represent a heterocyclic ring having 5, 6 or 7 atoms, which ring may contain carbon-carbon unsaturation.

2. The process of claim 1, wherein said thiol or sulphide is methyl mercaptan, ethyl mercaptan, propyl mercaptan, butyl mercaptan, amyl mercaptan, hexyl mercaptan, dimethyl sulphide, diethyl sulphide, dipropyl sulphide, dibutyl sulphide, diamyl sulphide, dihexyl sulphide, methyl ethyl sulphide, thiophen, tetrahydrothiophen, pentamethylene sulphide, cyclohexylmercaptan, benzyl mercaptan, thiophenol, dicyclohexyl sulphide, dibenzyl sulphide, diphenyl sulphide, ditolyl sulphide, thiodiglycol or thiomorpholine.

3. The process of claim 1 in which $R_1$ and $R_2$ represent alkyl groups having from 1 to 6 carbon atoms.

4. The process of claim 1 in which the sulphide is thiophen or a sulphide of the formula $R_1SR_2$ in which $R_1$ and $R_2$ together represent a tetramethylene or a pentamethylene group.

5. The process of claim 1 in which the organic thiol or sulphide is used in at least stoichiometric amount in relation to the copper.

6. The process of claim 1 in which the cuprous salt is dissolved in the minimum amount of thiol or sulphide.

7. A process as claimed in claim 1 for the manufacture of 3-pentenenitrile which comprises reacting butadiene with hydrogen cyanide in the mole ratio in the range 2:1 to 1:10 in the presence of a solution of from 0.0005 to 0.1 mole of cuprous chloride or cuprous bromide per mole of butadiene in an organic sulphide or thiol of the formula $R_1SH$ or $R_1SH_2$ in which $R_1$ and $R_2$, which in the case of sulphides may be the same or different, separately represent alkyl groups having from 1 6 carbon atoms or benzyl groups, or together represent tetramethylene or pentamethylene groups or with the S atom represent thiophen, at a temperature of 50° to 160°C, and separating the 3-pentenenitrile so formed.

* * * * *